United States Patent
Yang et al.

(10) Patent No.: US 11,759,138 B2
(45) Date of Patent: Sep. 19, 2023

(54) PHYSIOLOGICAL SIGNAL SENSING SYSTEM AND METHOD

(71) Applicant: Industrial Technology Research Institute, Hsinchu (TW)

(72) Inventors: Ming-Huan Yang, Hsinchu (TW); Yi-Cheng Lu, Hsinchu (TW); Yi-Wei Chung, New Taipei (TW); Kuang-Ching Fan, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 862 days.

(21) Appl. No.: 16/542,329

(22) Filed: Aug. 16, 2019

(65) Prior Publication Data

US 2020/0187808 A1 Jun. 18, 2020

(30) Foreign Application Priority Data

Dec. 12, 2018 (TW) .................................. 107144734

(51) Int. Cl.
*A61B 5/291* (2021.01)
*A61B 5/00* (2006.01)
(Continued)

(52) U.S. Cl.
CPC ............ *A61B 5/291* (2021.01); *A61B 5/0006* (2013.01); *A61B 5/0008* (2013.01);
(Continued)

(58) Field of Classification Search
CPC ..... A61B 5/291; A61B 5/0006; A61B 5/0008; A61B 5/02405; A61B 5/02438;
(Continued)

(56) References Cited

U.S. PATENT DOCUMENTS

| 6,625,481 B2 | 9/2003 | Bennett et al. |
| 2011/0125002 A1 | 5/2011 | Ershov et al. |

(Continued)

FOREIGN PATENT DOCUMENTS

| CN | 1736326 | 2/2006 |
| CN | 103002800 | 3/2013 |

(Continued)

OTHER PUBLICATIONS

"Office Action of Taiwan Counterpart Application," dated Nov. 13, 2019, p. 1-p. 16.

(Continued)

*Primary Examiner* — May A Abouelela
*Assistant Examiner* — Justin Xu
(74) *Attorney, Agent, or Firm* — JCIPRNET

(57) ABSTRACT

A physiological signal sensing system and a physiological signal sensing method are provided. The physiological signal sensing system includes a signal processing device and a physiological signal sensing device having a plurality of sensing electrodes. The sensing electrodes are used to contact the skin of an organism to sense a plurality of physiological signals. The signal processing device is coupled to the physiological signal sensing device to receive the physiological signals, compares these physiological signals with the reference physiological signal pattern to obtain a comparison result, selects a selected electrode pair from the sensing electrodes based on the comparison result, and uses the selected electrode pair to perform physiological signal measurement on the organism during a normal operation period.

8 Claims, 4 Drawing Sheets

(51) Int. Cl.
*A61B 5/389* (2021.01)
*A61B 5/024* (2006.01)
*A61B 5/318* (2021.01)
*A61B 5/369* (2021.01)

(52) U.S. Cl.
CPC .......... *A61B 5/02405* (2013.01); *A61B 5/389* (2021.01); *A61B 5/02438* (2013.01)

(58) Field of Classification Search
CPC ......... A61B 5/389; A61B 5/318; A61B 5/369; A61B 5/7221; A61B 5/4519; A61B 5/4851; A61B 5/6801; A61B 5/0015; A61B 2562/0209
See application file for complete search history.

(56) References Cited

U.S. PATENT DOCUMENTS

| | | | | |
|---|---|---|---|---|
| 2011/0295096 | A1* | 12/2011 | Bibian | A61B 5/291 600/372 |
| 2013/0109985 | A1* | 5/2013 | Gillberg | A61B 5/363 600/509 |
| 2014/0135643 | A1* | 5/2014 | Nierenberg | A61B 5/7203 600/300 |
| 2014/0187995 | A1* | 7/2014 | Hu | A61B 5/296 600/546 |
| 2014/0257129 | A1 | 9/2014 | Choi et al. | |
| 2015/0272457 | A1 | 10/2015 | Etemad et al. | |
| 2015/0282768 | A1* | 10/2015 | Luna | A61B 5/0205 600/386 |
| 2016/0051182 | A1 | 2/2016 | Zabaleta Rekondo et al. | |
| 2017/0086699 | A1 | 3/2017 | Shirai | |
| 2017/0095176 | A1* | 4/2017 | Sun | A61B 5/7225 |
| 2018/0317848 | A1* | 11/2018 | Gunasekar | A61B 5/291 |

FOREIGN PATENT DOCUMENTS

| | | |
|---|---|---|
| CN | 103164025 | 6/2013 |
| CN | 106175751 | 12/2016 |
| CN | 107073257 | 8/2017 |
| CN | 108261274 | 7/2018 |
| TW | 201427646 | 7/2014 |

OTHER PUBLICATIONS

"Office Action of Taiwan Counterpart Application", dated Jul. 5, 2019, pp. 1-14.

"Office Action of China Counterpart Application", dated Jul. 13, 2022, p. 1-p. 15.

* cited by examiner

PHYSIOLOGICAL SIGNAL SENSING SYSTEM AND METHOD

CROSS-REFERENCE TO RELATED APPLICATION

This application claims the priority benefits of Taiwan application serial no. 107144734, filed on Dec. 12, 2018. The entirety of the above-mentioned patent application is hereby incorporated by reference herein.

BACKGROUND

Technical Field

The disclosure relates to a physiological signal sensing system and a method thereof.

Description of Related Art

According to a biomedical measurement technology applied to a wearable device, physiological signal detection equipment (for instance, a sensing electrode pad or a sensor) may be worn on the body of a wearer, and various physiological signals of the wearer may be sensed in a non-invasive manner. For instance, a typical physiological signal measuring device senses the electromyography (EMG) signal of a specific muscle bundle by attaching the sensing electrode pad (or the sensor) to the wearer's skin. Since the general user does not understand the position of the muscle, the sensing electrode pad cannot be correctly attached to the correct muscle position, so that the EMG signal is distorted.

Furthermore, the sensing electrode pad (or the sensor) that needs to be in close contact with the wearer's skin often tends to warp, fall off, or the like. The sensing electrode pad (or the sensor) of a general physiological signal measurement device usually needs to be in close contact with the wearer's skin for obtaining an accurate physiological signal. However, due to the sweat generated by the wearer's skin, or the pulling due to the action, or due to other factors, a part or the whole of the sensing electrode pad (or the sensor) may be warped, fall off, and so on, so that the sensing electrode pad (or the sensor) fails to cling to the wearer's skin, thus causing the measured physiological signal to be distorted. The solution of the related art is generally to enhance the adhesion of the sensing electrode pad to enhance the adhesion that secures the sensing electrode pad firmly to the skin. However, this solution usually makes the wearer more uncomfortable (the sensing electrode pad falls off is still possible), or the arrangement of the sensing electrode pad becomes more inconvenient. Also, in many situations, the wearer is not aware that the sensing electrode pad has fallen off and the physiological signal has been distorted, resulting in poor accuracy of the physiological signal.

SUMMARY

According to an embodiment of the disclosure, a physiological signal sensing system is provided. The physiological signal sensing system includes a physiological signal sensing device and a signal processing device. The physiological signal sensing device includes a plurality of sensing electrodes. The sensing electrodes are used to contact a skin of an organism to sense at least one physiological signal. The signal processing device is coupled to the physiological signal sensing device to receive the at least one physiological signal. The signal processing device compares the at least one physiological signal with a reference physiological signal pattern to obtain a comparison result. The signal processing device selects a selected electrode pair from the sensing electrodes based on the comparison result. The signal processing device uses the selected electrode pair to perform a physiological signal measurement on the organism during a normal operation period.

According to an embodiment of the disclosure, a physiological signal sensing method is provided. The physiological signal sensing method includes: sensing at least one physiological signal of an organism by a plurality of sensing electrodes of a physiological signal sensing device, comparing the at least one physiological signal with a reference physiological signal pattern to obtain a comparison result by the signal processing device, selecting a selected electrode pair from the sensing electrodes based on the comparison result by the signal processing device, and performing a physiological signal measurement on the organism by using the selected electrode pair during a normal operation period by the signal processing device.

According to an embodiment of the disclosure, a physiological signal sensing system is provided. The physiological signal sensing system includes a physiological signal sensing device and a signal processing device. The physiological signal sensing device includes a plurality of sensing electrodes. The sensing electrodes are used to contact a skin of an organism to sense at least one physiological signal. The signal processing device is coupled to the physiological signal sensing device to receive the at least one physiological signal. The signal processing device sorts a part or all of the sensing electrodes according to the at least one physiological signal to determine a selection order. The signal processing device selects a first sensing electrode of a first order in the selection order and a second sensing electrode of a second order in the selection order as a selected electrode pair. The signal processing device uses the selected electrode pair to perform a physiological signal measurement on the organism during a normal operation period. When a first signal feature of the first sensing electrode or a second signal feature of the second sensing electrode is lower than a third signal feature of a third sensing electrode of a third order in the selection order, the signal processing device selects the third sensing electrode to replace the first sensing electrode or the second sensing electrode.

The foregoing will become better understood from a careful reading of a detailed description provided herein below with appropriate reference to the accompanying drawings.

DESCRIPTION OF THE EMBODIMENTS

Figure 1:
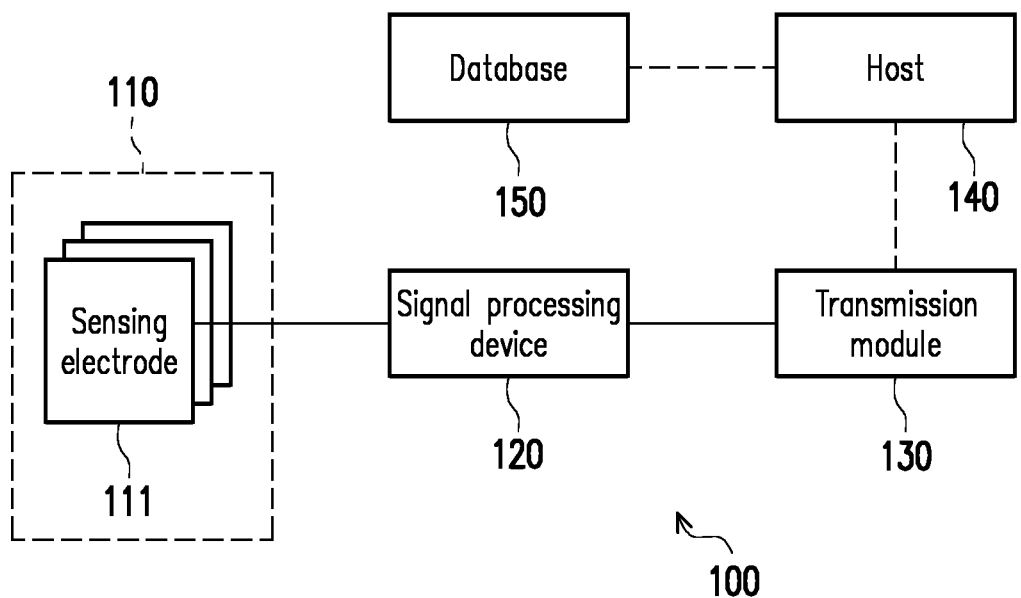
FIG. 1 is a schematic diagram showing a circuit block of a physiological signal sensing system according to an embodiment of the disclosure.

Wording such as up, down, front, back, left and right mentioned in exemplary embodiments merely refers to the directions in the accompanying drawings without being limited to the exemplary embodiments set forth herein.

The term "coupling/coupled" used in this specification (including claims) may refer to any direct or indirect connection means. For example, "a first device is coupled to a second device" may be interpreted as "the first device is directly connected to the second device" or "the first device is indirectly connected to the second device through other devices or connection means". Descriptions of well-known parts are omitted for clarity, and like reference numerals refer to like elements throughout.

FIG. 1 is a schematic diagram showing a circuit block of a physiological signal sensing system according to an embodiment of the disclosure. The physiological signal sensing system 100 includes a physiological signal sensing device 110, a signal processing device 120, a transmission module 130, a host 140 and a database 150. In an embodiment, the transmission module 130, the host 140 and/or the database 150 may be omitted according to the design requirements. For instance, in the case where the signal processing device 120 and the host 140 are integrated into a same local device, the transmission module 130 may be omitted. That is, the signal processing device 120 may be directly coupled to the host 140, or the signal processing device 120 may be integrated into host 140. In another embodiment, the function of the host 140 can be integrated into the signal processing device 120. Therefore, the transmission module 130 and the host 140 shown in FIG. 1 may be omitted, that is, the database 150 may be directly coupled to the signal processing device 120. In yet another embodiment, the functions of the host 140 and the database 150 may be integrated into the signal processing device 120. Therefore, the transmission module 130, the host 140, and the database 150 shown in FIG. 1 may be omitted.

In the embodiment of FIG. 1, the physiological signal sensing device 110 includes a plurality of sensing electrodes 111. These sensing electrodes 111 are disposed at different positions of the physiological signal sensing device 110. The material of the physiological signal sensing device 110 and/or the sensing electrodes 111 may include at least one shapeable material or at least one flexible material. The sensing electrodes 111 are used to contact a skin of an organism (for example, body, a limb or head of a human or an animal, and so on) to sense a plurality of physiological signals at different positions of the organism.

Figure 2:
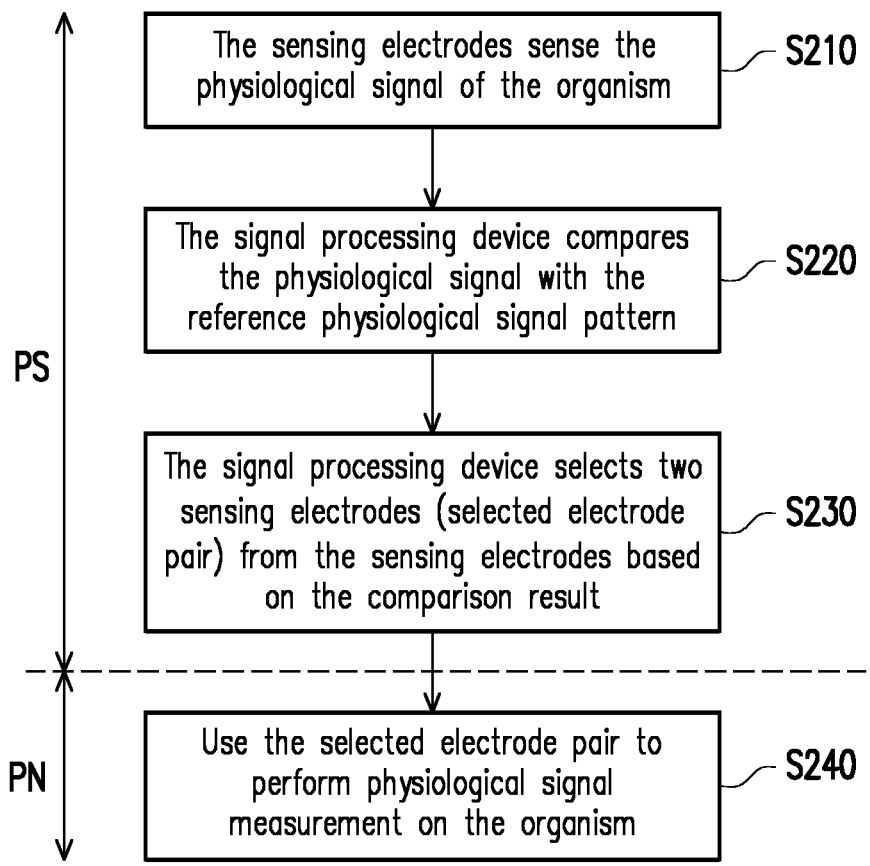
FIG. 2 is a flowchart of a physiological signal sensing method according to an embodiment of the disclosure.

FIG. 2 is a flowchart of a physiological signal sensing method according to an embodiment of the disclosure. Please refer to FIG. 1 and FIG. 2. In step S210, the sensing electrodes 111 of the physiological signal sensing device 110 are used to contact a skin of an organism (for example, body, a limb or head of a human or an animal etc.) to sense at least one physiological signal at different positions of the organism. The signal processing device 120 is coupled to the physiological signal sensing device 110 to receive the at least one physiological signal of the sensing electrodes 111. According to the at least one physiological signal, the signal processing device 120 selects an electrode pair (hereinafter referred to as a selected electrode pair) from the sensing electrodes 111 automatically. That is, the signal processing device 120 can automatically find a target position (for instance, the position of a specific muscle bundle of the organism). Therefore, during a normal operation period PN, the signal processing device 120 can use the selected electrode pair to perform a physiological signal measurement on the organism to obtain a physiological signal of the specific muscle bundle of the organism.

According to the design requirements, the physiological signal provided in the embodiment may be a body temperature, a pulse, a heart rate, a respiratory rate, a dynamic myoelectric current value, an electroencephalography (EEG), an electromyography (EMG), an electroneurogram (ENG), an electroretinogram (ERG), an electrogastrogram (EGG), an electroneuromyography (ENMG), an electrocorticography (ECoG), an electrooculogram (EOG), an electronystagmography (ENG), or other physiological signals. For instance, these physiological signals include the EMG signal of the muscle bundle of the organism.

The transmission module 130 may connect with the host 140 through any communication network (cable and/or wireless network). During the normal operation period, the signal processing device 120 can transmit the physiological signal of the selected electrode pair to the host 140 via the transmission module 130. After the host 140 obtains the physiological signal, the physiological signal is subjected to data computation to obtain a calculated physiological value. For instance, the host 140 may present the physiological signal on a display (not shown) of the host 140 in form of tables, images, and/or specific user interfaces, so that a user is able to learn the value of his/her physiological signal values and the variations thereof. In an embodiment, the host 140 may be a consumer computing device (for instance, a notebook computer, a tablet, a smart phone or other computing devices). In other embodiments, the host 140 may be a cloud server (also referred to as a cloud computing platform). The host 140 can use a display to present the wearer's physiological signal values, such as wearer's body temperature, the pulse, the heart rate, the respiratory rate, the dynamic myoelectric current value or other physiological signal values. In an embodiment, the host 140 also can circulate the wearer's physiological conditions, such as wearer's muscle endurance, muscle strength, muscle fatigue, physical condition, exercise cycle, health condition, abnormal warnings or other physiological conditions.

After the physiological signal sensing system 100 performs the physiological signal measurement on the organism, the physiological signal sensing system 100 can obtain corresponding physiological sensing results. This embodiment does not limit the application of the physiological sensing result. For instance, in some applications, the physiological sensing results can be applied to the manipulation of an active prosthetic. The host 140 can correspondingly control/drive the joint motor of the active prosthetic according to the physiological signal of the selected electrode pair (for example, the EMG signal of the muscle bundle).

In the embodiment shown in FIG. 1, the database 150 may store one or more reference patterns. The signal processing device 120 can select a reference pattern (hereinafter referred to as a reference physiological signal pattern) from the reference patterns of the database 150 according to a target condition. For instance, these reference patterns may include reference patterns of EMG signals of different muscle bundles of the human body. Under the application condition (target condition) that the target muscle bundle is named by "muscle bundle A", the signal processing device 120 can select the reference pattern of "muscle bundle A" from the reference patterns of the database 150 as the reference physiological signal pattern. The target condition can be set by the host 140.

In step S220, the signal processing device 120 may compare the at least one physiological signal of the sensing electrodes 111 with the reference physiological signal pattern to obtain a comparison result. In step S230, the signal processing device 120 selects two sensing electrodes (selected electrode pair) from the sensing electrodes based on the comparison result. The step S210, step S220 and step S230 may be performed during a non-normal operation period (for instance, an electrode selection period PS). In step S240, the signal processing device 120 may use the selected electrode pair to perform the physiological signal measurement on the organism during the normal operation period PN.

The method of operation of the physiological signal sensing system 100 (physiological signal sensing method) shown in FIG. 1 should not be limited to the embodiment of FIG. 2. For instance, in other embodiments, the physiological signal sensing system 100 may also include a guiding device (not shown), such as a smart phone, a smart watch, or other electronic devices. Based on the guidance data of the database 150, the guiding device can guide/instruct the user to wear the physiological signal sensing device 110 (sensing electrodes 111) by using the sound, video, and/or other guiding means. After the user wears the physiological signal sensing device 110 (the sensing electrode 111), the signal processing device 120 can perform steps S210 to step S240. In step S210, the guiding device (not shown) can also guide/instruct the user to perform a specific gesture and/or action, so that the signal processing device 120 senses the physiological signal of the user (the wearer) via the sensing electrodes 111. The muscle bundle used (corresponding) for the actions has been recorded in the database 150, so the position of the sensing electrodes having the largest signal feature (e.g., signal intensity, frequency, strength, etc.) among the sensing electrodes 111 is the position of the target muscle, and the sensing electrodes having the largest signal feature are also the preferred selected electrode pair. Therefore, the signal processing device 120 may use the selected electrode pair to perform the physiological signal measurement of the user during the normal operation period PN.

According to design requirements, the physiological signal sensing device 110 may have a reference electrode in addition to the plurality of sensing electrodes 111. The signal processing device 120 can transmit a reference signal (or a driving signal) to the organism via the reference electrode, so that the physiological signal measurement on the organism is performed via the plurality of sensing electrodes. The reference electrode may be disposed at any position of the physiological signal sensing device 110 according to design requirements. For instance, but not limited to, the reference electrode may be disposed at a central position of the physiological signal sensing device 110, and the plurality of sensing electrodes are located around the reference electrode.

Figure 3:
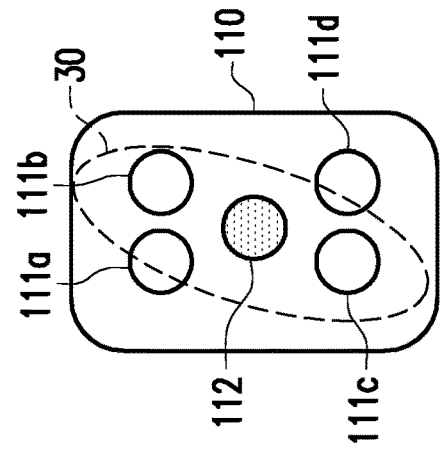
FIG. 3 is a schematic diagram showing a layout of a physiological signal sensing device according to an embodiment of the disclosure.

FIG. 3 is a schematic diagram showing a layout of a physiological signal sensing device according to an embodiment of the disclosure. Please refer to FIG. 1 and FIG. 3. The physiological signal sensing device 110 shown in FIG. 3 includes a sensing electrode 111a, a sensing electrode 111b, a sensing electrode 111c, a sensing electrode 111d, and a reference electrode 112. The reference electrode 112 is disposed at a central position of the physiological signal sensing device 110, and the sensing electrodes 111a to 111d are located around the reference electrode 112. The sensing electrodes 111a to 111d are divided into a first sensing electrode group and a second sensing electrode group. For instance, the sensing electrode 111a and the sensing electrode 111b are classified into the first sensing electrode group, and the sensing electrode 111c and the sensing electrode 111d are classified into the second sensing electrode group. The first sensing electrode group is located on a first side of the reference electrode 112, and the second sensing electrode group is located on a second side of the reference electrode 112 (the first side and the second side are opposite sides of each other).

After the physiological signal sensing device 110 is worn on (or pasted to) the organism, the signal processing device 120 can transmit the reference signal (or driving signal) to the organism via the reference electrode 112. The sensing electrodes 111a to 111d can sense a plurality of physiological signals at different positions of the organism (for example, body, limb or head of a human or an animal) (step S210). In the embodiment shown in FIG. 3, the physiological signal sensing device 110 has a muscle bundle 30 (target muscle bundle) in the coverage. The signal processing device 120 selects a reference pattern of the muscle bundle 30 from a plurality of reference patterns of the database 150 (hereinafter referred to as a reference physiological signal pattern).

The signal processing device 120 compares these physiological signals of the sensing electrodes 111a to 111d with the reference physiological signal pattern of the muscle bundle 30 to obtain a comparison result (step S220). The signal processing device 120 selects two sensing electrodes (a selected electrode pair) from the sensing electrodes 111a to 111d based on the comparison result (step S230). For instance, the signal processing device 120 compares these physiological signals of the sensing electrodes 111a to 111d with the reference physiological signal pattern of the muscle bundle 30 to selects a first selected electrode from the first sensing electrode group and a second selected electrode from the second sensing electrode group. Because a partial area of the sensing electrode 111a is beyond the muscle bundle 30, so the signal feature (e.g., signal intensity, frequency, strength, etc.) of the sensing electrode 111a is smaller than the signal feature (e.g., signal intensity, frequency, strength, etc.) of the sensing electrode 111b, even the similarity between the physiological signal of the sensing electrode 111a and the reference physiological signal pattern is less than that between the physiological signal of the sensing electrode 111b and the reference physiological signal pattern. Therefore, the signal processing device 120 may select the sensing electrode 111b as the first selected electrode. Similarly, the signal processing device 120 may select the sensing electrode 111c as the second selected electrode. The sensing electrode 111b (the first selected electrode) and the sensing electrode 111c (the second selected electrode) may serve as the selected electrode pair.

The signal processing device 120 can automatically find the target position (for instance, the position of the muscle bundle 30), that is, two sensing electrodes of the sensing electrodes 111a to 111d corresponding to the positions of the muscle bundle 30 are selected as the selected electrode pair. The signal processing device 120 can use the selected electrode pair (the sensing electrode 111b and the sensing electrode 111c) to perform the physiological signal measurement of the muscle bundle 30 of the organism during the normal operation period PN (step S240).

It is considered that any of the sensing electrodes 111a to 111d may be warped or fall off during the normal operation period PN. When any of the sensing electrodes of the selected electrode pair is warped or falls off, the measured physiological signals of the selected electrode pair may be distorted (or the precision is not good). Therefore, in an embodiment, when at least one of the measured physiological signals of the selected electrode pair is abnormal (for instance, the signal strength of at least one of the measured physiological signals is lower than a predetermined threshold value), the signal processing device 120 can perform the steps S210 to S230 shown in FIG. 2 again to find a new selected electrode pair from the sensing electrodes 111a to 111d.

Figure 4:
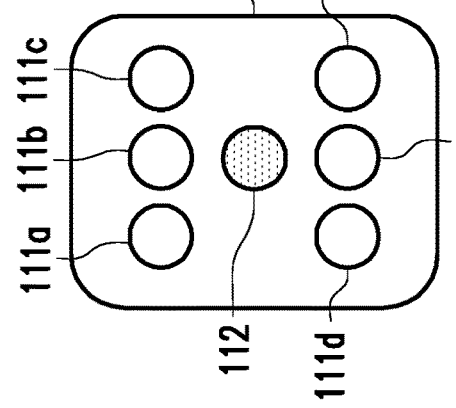
FIG. 4 is a schematic diagram showing a layout of a physiological signal sensing device according to another embodiment of the disclosure.

FIG. 4 is a schematic diagram showing a layout of a physiological signal sensing device 110 according to another embodiment of the disclosure. Please refer to FIG. 1 and FIG. 4. The physiological signal sensing device 110 shown in FIG. 4 includes the sensing electrode 111a, the sensing electrode 111b, the sensing electrode 111c, the sensing electrode 111d, a sensing electrode 111e, a sensing electrode 111f and the reference electrode 112. The reference electrode 112 is disposed at a central position of the physiological signal sensing device 110, and the sensing electrodes 111a to 111f are located around the reference electrode 112. According to design requirement, the sensing electrodes 111a to 111f are divided into a first sensing electrode group and a second sensing electrode group. For instance, the sensing electrodes 111a to 111c are classified into a first sensing electrode group, and the sensing electrodes 111d to 111f are classified into a second sensing electrode group. The first sensing electrode group is located on the first side of the reference electrode 112, and the second sensing electrode group is located on the second side of the reference electrode 112 (the first side and the second side are opposite sides of each other). The physiological signal sensing device 110 shown in FIG. 4 can be analogized with reference to the related description of FIG. 3, so the description thereof is omitted.

Figure 5:
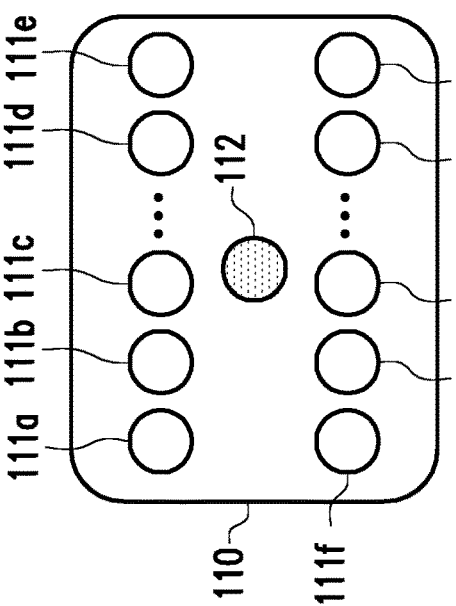
FIG. 5 is a schematic diagram showing a layout of a physiological signal sensing device according to yet another embodiment of the disclosure.

According to design requirements, the physiological signal sensing device 110 may include more sensing electrodes. FIG. 5 is a schematic diagram showing a layout of a physiological signal sensing device according to yet another embodiment of the disclosure. Please refer to FIG. 1 and FIG. 5. The physiological signal sensing device 110 shown in FIG. 5 includes a first sensing electrode group, a second sensing electrode group and the reference electrode 112. The first sensing electrode group includes the sensing electrode 111a, the sensing electrode 111b, the sensing electrode 111c, to the sensing electrode 111d and the sensing electrode 111e. The second sensing electrode group includes the sensing electrode 111f, a sensing electrode 111g, a sensing electrode 111h, to a sensing electrode 111i and a sensing electrode 111j. The reference electrode 112 is disposed at a central position of the physiological signal sensing device 110. The first sensing electrode group is located on the first side of the reference electrode 112, and the second sensing electrode group is located on the second side of the reference electrode 112 (the first side and the second side are opposite sides of each other). The physiological signal sensing device 110 shown in FIG. 5 can be analogized with reference to the related description of FIG. 3, so the description thereof is omitted.

Figure 6:
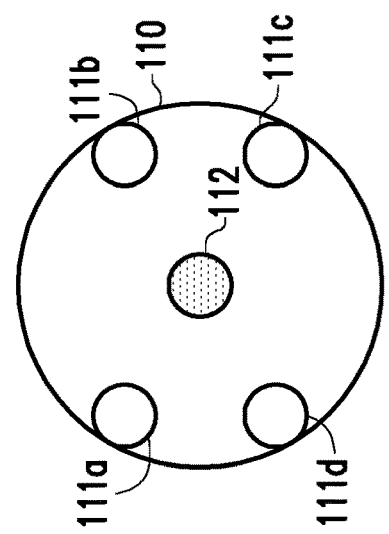
FIG. 6 is a schematic diagram showing a layout of a physiological signal sensing device according to yet another embodiment of the disclosure.

FIG. 6 is a schematic diagram showing a layout of a physiological signal sensing device according to yet another embodiment of the disclosure. Please refer to FIG. 1 and FIG. 6. The physiological signal sensing device 110 shown in FIG. 6 includes the sensing electrode 111a, the sensing electrode 111b, the sensing electrode 111c, the sensing electrode 111d and the reference electrode 112. The reference electrode 112 is disposed at a central position of the physiological signal sensing device 110, and the sensing electrodes 111a to 111d are located around the reference electrode 112.

After the physiological signal sensing device 110 is worn on (or pasted to) the organism, the signal processing device 120 can transmit the reference signal (or driving signal) to the organism via the reference electrode 112 shown in FIG. 6. The sensing electrodes 111a to 111d shown in FIG. 6 can sense a plurality of physiological signals at different positions of the organism (for example, body, limb or head of a human or an animal) (step S210). In the embodiment shown in FIG. 6, the signal processing device 120 compares these physiological signals of the sensing electrodes 111a to 111d with the reference physiological signal pattern (step S220) in order to select a plurality of candidate physiological signals from these physiological signals. For instance (but not limited to), the signal processing device 120 can obtain the similarity of the physiological signal of each sensing electrode by comparing any of the physiological signals of the sensing electrodes 111a to 111d with the reference physiological signal pattern. When the similarity of the physiological signal of the sensing electrode 111a is greater than the said threshold value, the physiological signal of the sensing electrode 111a can be selected as a candidate physiological signal. In other words, the physiological signal having the similarity greater than the threshold value is selected as a candidate physiological signal. Similarly, other sensing electrodes 111b to 111d can be analogized with reference to the related description of the sensing electrodes 111a, and therefore the description thereof is omitted. The threshold value can be determined according to design requirements. For instance, in an embodiment, the threshold value may be 80%. In other embodiments, the threshold value may be 90% or other values.

The signal processing device 120 can select two candidate physiological signals having the maximum and a second largest signal strengths, respectively, from the candidate physiological signals as two selected signals. The signal processing device 120 may select the two sensing electrodes from the sensing electrodes 111a to 111d corresponding to the two selected signals as the selected electrode pair (step S230). The signal processing device 120 can automatically find a target position (for instance, the position of the muscle bundle), that is, the two sensing electrodes of the sensing electrodes 111a to 111d corresponding to the positions of the muscle bundle, respectively, are selected as the selected electrode pair. The signal processing device 120 can use the selected electrode pair to perform the physiological signal measurement of the muscle beam of the organism during a normal operation period PN (step S240).

It is considered that any of the sensing electrodes 111a to 111d may be warped or fall off during the normal operation period PN. When any of the sensing electrodes of the selected electrode pair is warped, or fall off, the measured physiological signals of the selected electrode pair may be distorted (or the precision is not good). Therefore, in some embodiments, when at least one of the measured physiological signals of the selected electrode pair is abnormal (for instance, the signal strength of at least one of the measured physiological signals is lower than a predetermined threshold value), The signal processing device 120 can perform the steps S210 to S230 shown in FIG. 2 again to find a new selected electrode pair from the sensing electrodes 111a to 111d.

In other embodiments, after the physiological signal sensing device 110 is worn on (or pasted to) the organism, the signal processing device 120 can sense/collect a plurality of physiological signals at different positions of the organism (for example, body, limb or head of a human or an animal) via the sensing electrodes 111a to 111d. The signal processing device 120 compares these physiological signals of the sensing electrodes 111a to 111d with the reference physiological signal pattern in order to select a plurality of candidate physiological signals from these physiological signals. Then, according to the signal features (e.g., signal intensity, frequency, strength, etc.) of the candidate physiological signals, the signal processing device 120 may sort the plurality of candidate electrodes corresponding to the plurality of candidate physiological signals of the sensing electrodes 111a to 111d to determine a selection order of the candidate electrodes. The signal processing device 120 may select a first order candidate electrode (hereinafter referred to as a first candidate electrode) in the selection order and a second order candidate electrode (hereinafter referred to as a second candidate electrode) in the selection order as the selected electrode pair. During the normal operation period PN, when the signal feature (e.g., signal strength, intensity, frequency, etc.) of the first candidate electrode is lower than the signal feature (e.g., signal strength, intensity, frequency, etc.) of a third order candidate electrode (hereinafter referred to as a third candidate electrode) in the selected order, the signal processing device 120 can select the third candidate electrode to replace the first candidate electrode to obtain a new selected electrode pair. When the signal feature (e.g., signal strength, intensity, frequency, etc.) of the second candidate electrode is lower than the signal feature (e.g., signal strength, intensity, frequency, etc.) of the third candidate electrode, the signal processing device 120 can select the third candidate electrode to replace the second candidate electrode to obtain a new selected electrode pair. Similarly, when the signal feature (e.g., signal strength, intensity, frequency, etc.) of any electrode of the selected electrode pairs (for instance, the third candidate electrode) is lower than the signal feature (e.g., signal strength, intensity, frequency, etc.) of the fourth order candidate electrode (hereinafter referred to as a fourth candidate electrode) in the selected order, the signal processing device 120 can select the fourth candidate electrode to replace the third candidate electrode to obtain another new selected electrode pair.

Figure 7:
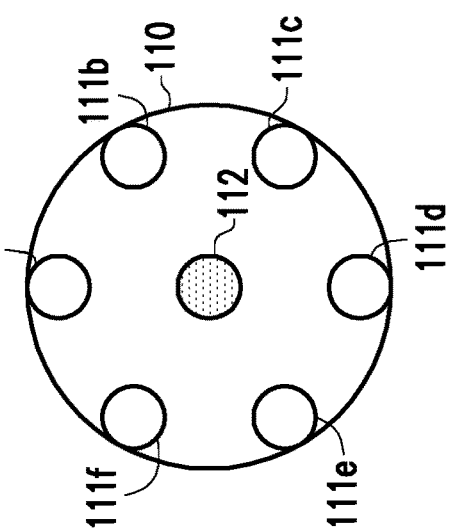
FIG. 7 is a schematic diagram showing a layout of a physiological signal sensing device according to yet another embodiment of the disclosure.

FIG. 7 is a schematic diagram showing a layout of a physiological signal sensing device according to yet another embodiment of the disclosure. Please refer to FIG. 1 and FIG. 7. The physiological signal sensing device 110 shown in FIG. 7 includes the sensing electrode 111a, the sensing electrode 111b, the sensing electrode 111c, the sensing electrode 111d, the sensing electrode 111e, the sensing electrode 111f and the reference electrode 112. The reference electrode 112 is disposed at a central position of the physiological signal sensing device 110, and the sensing electrodes 111a to 111f are located around the reference electrode 112. The physiological signal sensing device 110 shown in FIG. 7 can be analogized with reference to the related description of FIG. 6, so the description thereof is omitted.

Figure 8:
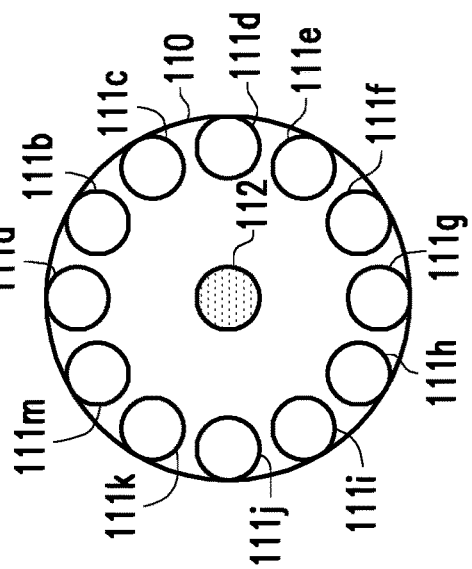
FIG. 8 is a schematic diagram showing a layout of a physiological signal sensing device according to yet another embodiment of the disclosure.

According to design requirements, the physiological signal sensing device 110 may include more sensing electrodes. FIG. 8 is a schematic diagram showing a layout of a physiological signal sensing device according to yet another embodiment of the disclosure. Please refer to FIG. 1 and FIG. 8. The physiological signal sensing device 110 shown in FIG. 8 includes the sensing electrode 111a, the sensing electrode 111b, the sensing electrode 111c, the sensing electrode 111d, the sensing electrode 111e, the sensing electrode 111f, the sensing electrode 111g, the sensing electrode 111h, the sensing electrode 111i, the sensing electrode 111j, a sensing electrode 111k, a sensing electrode 111m and the reference electrode 112. The reference electrode 112 is disposed at a central position of the physiological signal sensing device 110, and the sensing electrodes 111a to 111m are located around the reference electrode 112. The physiological signal sensing device 110 shown in FIG. 8 can be analogized with reference to the related description of FIG. 6, so the description thereof is omitted.

The reference electrode 112 shown in FIG. 3 to FIG. 8 is disposed at a central position of the physiological signal sensing device 110, but the scope of the disclosure is not limited thereto. In other embodiments, the reference electrode 112 may also be configured at a non-central position of the physiological signal sensing device 110.

Figure 9:
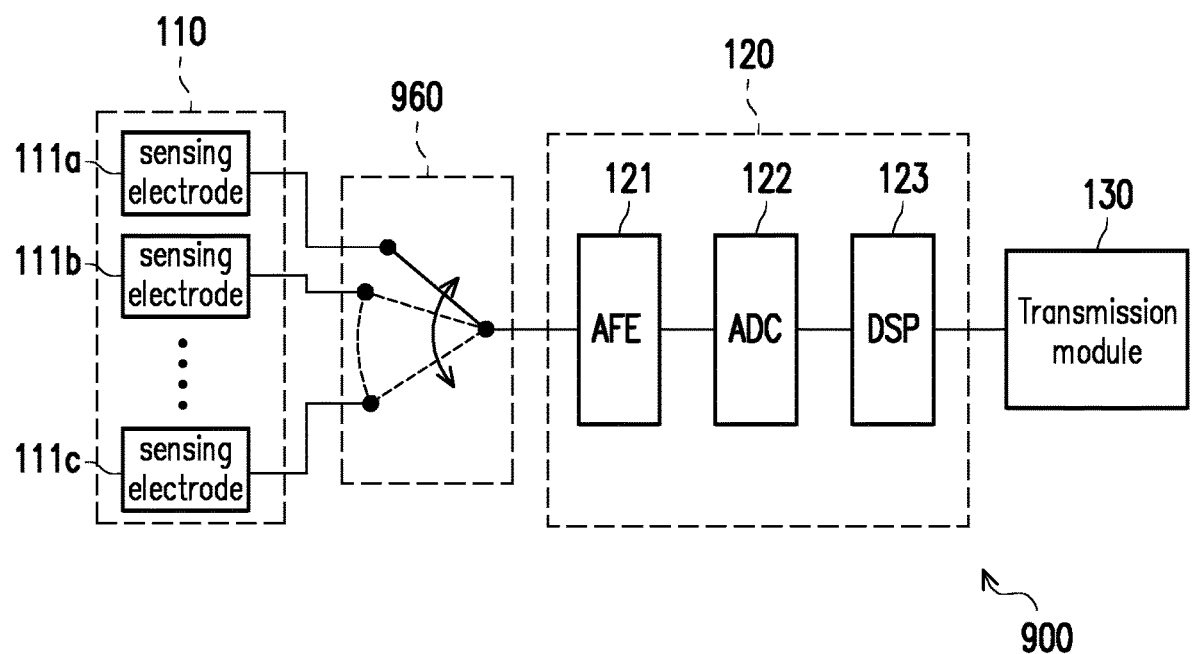
FIG. 9 is a schematic diagram showing a circuit block of a physiological signal sensing system according to another embodiment of the disclosure.

FIG. 9 is a schematic diagram showing a circuit block of a physiological signal sensing system according to another embodiment of the disclosure. In the embodiment shown in FIG. 9, the physiological signal sensing system 900 includes the physiological signal sensing device 110, a switch 960, the signal processing device 120, and the transmission module 130. The physiological signal sensing device 110, the signal processing device 120 and the transmission module 130 shown in FIG. 9 can be analogized with reference to the related description of FIG. 1 to FIG. 8, so the description thereof is omitted. According to the design requirements, the host 140 and/or the database 150 shown in FIG. 1 can be configured in the physiological signal sensing system 900.

Please refer to FIG. 9, the switch 960 is coupled to the physiological signal sensing device 110 to select one sensing electrode from the first sensing electrode group or one sensing electrode from the second sensing electrode group. In the embodiment shown in FIG. 9, the physiological signal sensing device 110 includes the sensing electrode 111a, the sensing electrode 111b, and the sensing electrode 111c. The switch 960 can select one sensing electrode from the sensing electrodes 111a to 111c. The switch 960 electrically connects the selected sensing electrodes to the signal processing device 120. In an embodiment, the signal processing device 120 can receive the physiological signals of the sensing electrodes 111a to 111c via the switch 960 in a manner of time division multiplexing.

In the embodiment shown in FIG. 9, the signal processing device 120 includes an analog front end (AFE) circuit 121, an analog-to-digital converter (ADC) 122 and a digital signal processor (DSP) 123. After the sensing electrodes 111a to 111c are worn on (or pasted to) the organism, the digital signal processor 123 can obtain a digital values of the physiological signals of the sensing electrodes 111a to 111c via the switch 960, the analog front end circuit 121 and the analog-to-digital converter 122. The digital signal processor 123 can perform steps S210 to S240 shown in FIG. 2 to obtain a digital value of the physiological signal of the target muscle bundle of the organism. The digital signal processor 123 can transmit these digital values to other devices (for instance, the host 140 shown in FIG. 1) via the transmission module 130.

Figure 10:
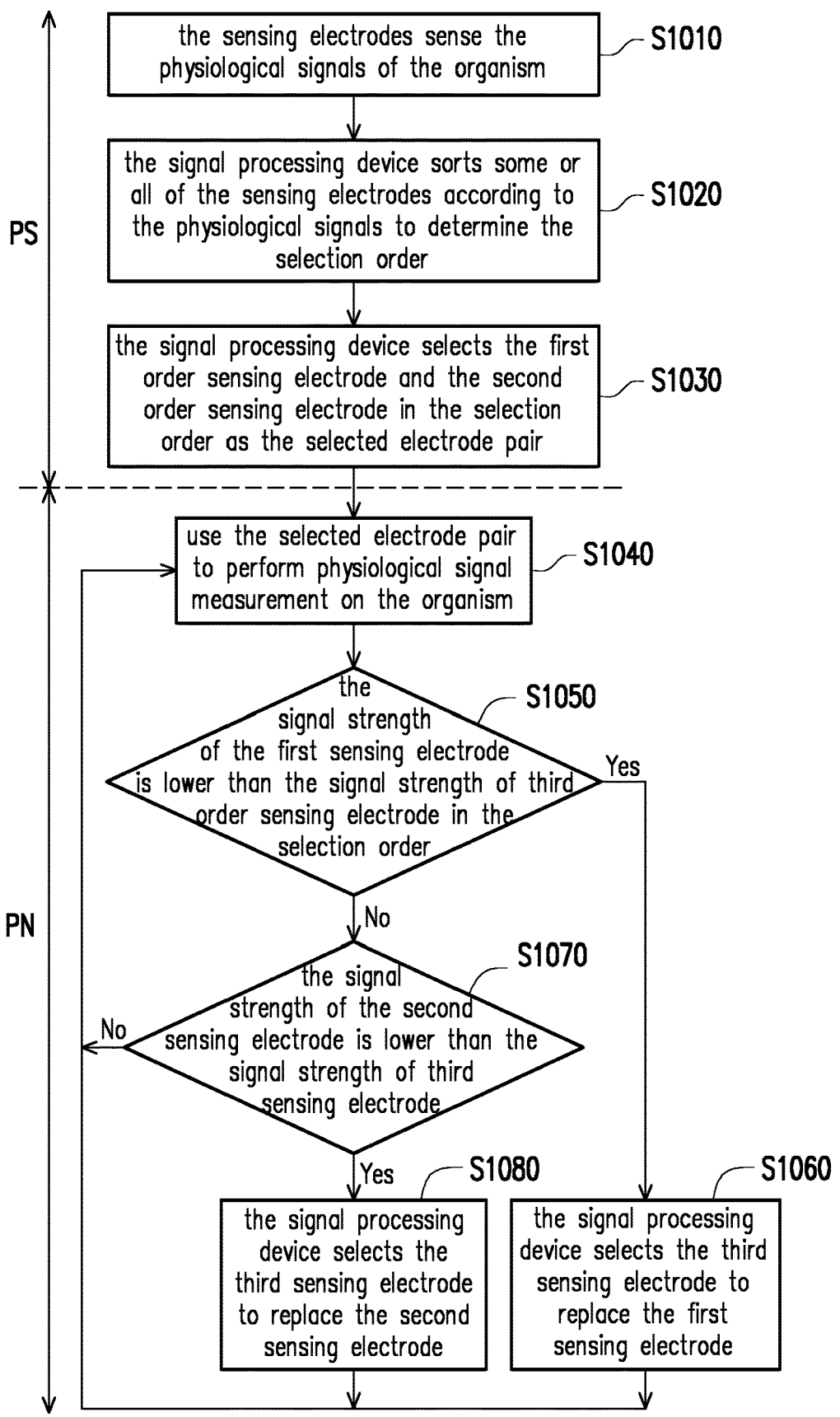
FIG. 10 is a flowchart of a physiological signal sensing method according to another embodiment of the disclosure.

FIG. 10 is a flowchart of a physiological signal sensing method according to another embodiment of the disclosure. Please refer to FIG. 1 and FIG. 10. The physiological signal sensing device 110 includes the plurality of sensing electrodes 111. In step S1010, the sensing electrodes 111 may contact surfaces of different positions of an organism (for example, body, limb or head of a human or an animal) to sense a plurality of physiological signals at different positions. Step S1010 can be analogized with reference to the related description of Step 210, so the description thereof is omitted.

The signal processing device 120 is coupled to the physiological signal sensing device 110 to receive the physiological signals of the sensing electrodes 111. In step S1020, the signal processing device 120 may sort a part or all of the sensing electrodes 111 according to the physiological signals of the sensing electrodes 111 to determine the selection order. For instance, according to the signal strengths of the physiological signals of the sensing electrodes 111, the signal processing device 120 may sort the sensing electrodes 111 to determine the selection order of the sensing electrodes 111.

In step S1030, the signal processing device 120 may select a first order sensing electrode (hereinafter referred to as a first sensing electrode) in the selection order and a second order sensing electrode (hereinafter referred to as a second sensing electrode) in the selection order as the selected electrode pair. The step S1010, the step S1020, and the step S1030 may be performed during a non-normal operation (for instance, the electrode selection period PS). During the normal operation period PN, the signal processing device 120 can use the selected electrode pair to perform physiological signal measurement on the organism (step S1040).

When the signal feature (e.g., signal strength, intensity, frequency, etc.) of the first sensing electrode is lower than the signal feature (e.g., signal strength, intensity, frequency, etc.) of a third order sensing electrode (hereinafter referred to as a third sensing electrode) in the selection order (step S1050 is "Yes"), the signal processing device 120 can perform step S1060 to select the third sensing electrode to replace the first sensing electrode to obtain a new selected electrode pair. When step S1050 is "No", the signal processing device 120 can perform step S1070. When the signal strength (signal feature) of the second sensing electrode is lower than the signal strength (signal feature) of the third sensing electrode (step S1070 is "Yes"), the signal processing device 120 can perform step S1080 to select the third sensing electrode to replace the second sensing electrode to obtain a new selected electrode pair. When step S1070 is "No", the signal processing device 120 may perform step S1040 again, that is, the physiological signal measurement on the organism is performed by using the original selected electrode pair.

In summary, the physiological signal sensing system and method can automatically find a target position (for instance, the position of a target muscle bundle), according to the embodiments of the present disclosure. In an embodiment, a plurality of sensing electrodes sense a plurality of physiological signals of the organism, and then the signal processing device 120 compares the physiological signals with the reference physiological signal pattern to obtain a comparison result. The signal processing device 120 selects a selected electrode pair from the sensing electrodes based on the comparison result. The signal processing device 120 uses the selected electrode pair to perform physiological signal measurement on the organism during a normal operation period. Therefore, the physiological signal sensing system can automatically find the target position to perform physiological signal measurement on the organism.

In other embodiments, the signal processing device 120 sorts a part or all of the sensing electrodes according to the physiological signals of the sensing electrodes to determine a selection order. According to the selection order, the signal processing device 120 selects two sensing electrodes (the selected electrode pair) from the sensing electrodes. The signal processing device 120 uses the selected electrode pair to perform physiological signal measurement on the organism during the normal operation period PN. When at least one measured physiological signal of the selected electrode pair is abnormal (for instance, the signal strength of the at least one measured physiological signal is lower than a predetermined threshold value), the signal processing device 120 can select the next-order sensing electrode according to the selected order to obtain a new selected electrode pair. Next, the signal processing device 120 can use this new selected electrode pair to perform physiological signal measurement on the organism during the normal operation period PN.

According to the design requirements, the signal processing device 120, the transmission module 130, the host 140, the database 150, and/or the digital signal processor 123 may be implemented by hardware, firmware, software (program) or any combination of the foregoing three. Also, various numbers of the sensing electrodes can be made to the disclosed embodiments without departing from the scope or spirit of the disclosure. In other words, the number of the sensing electrodes can be a variable integer greater than one.

In the form of hardware, the signal processing device 120, the transmission module 130, the host 140, and/or the database 150 may be implemented in a logic circuit on an integrated circuit. The related functions of the signal processing device 120, the transmission module 130, the host 140 and/or the database 150 may be implemented as hardware by using hardware description languages (HDL) (such as Verilog HDL or very high speed integrated circuit (VHSIC) HDL) or other suitable programming languages. For instance, the functions of the signal processing device 120, the transmission module 130, the host 140, and/or the database 150 can be implemented in one or more controllers, microcontrollers, microprocessors, application-specific integrated circuit (ASIC), digital signal processor, Field Programmable Gate Array (FPGA), and/or various logic blocks, modules, and circuits in other processing units.

In the form of software and/or firmware, the functions of the signal processing device 120, the transmission module 130, the host 140, the database 150, and/or the digital signal processor 123 can be implemented as programming codes. For instance, the signal processing device 120, the transmission module 130, the host 140, the database 150, and/or the digital signal processor 123 are implemented by a general programming language (such as C, C++, or assembly language) or other suitable programming languages. The programming codes may be recorded/stored in a recording medium, and the recording medium includes, for instance, a read only memory (ROM), a storage device, and/or a random access memory (RAM). A computer, a central processing unit (CPU), a controller, a microcontroller or a microprocessor can read the programming codes from the recording medium and execute the programming codes to achieve a related function. As the recording medium, a non-transitory computer readable medium can be used. For instance, a tape, a disk, a card, a semiconductor memory, a programmable logic circuit, or the like can be used. Also, the programming codes can be provided to the computer (or CPU) via any transmission medium (communication network, broadcast wave, and so on). The communication network is, for instance, the Internet, wired communication, wireless communication or other communication media.

It will be apparent to those skilled in the art that various modifications and variations can be made to the disclosed embodiments without departing from the scope or spirit of the disclosure. It is intended that the specification and examples be considered as exemplars only, with a true scope of the disclosure being indicated by the following claims and their equivalents.

What is claimed is:

1. A physiological signal sensing system, comprising:
a physiological signal sensing device having a plurality of sensing electrodes and a reference electrode, and the plurality of sensing electrodes are located around the reference electrode, wherein the sensing electrodes are used to contact a skin of an organism to sense at least one physiological signal, and the plurality of sensing electrodes are divided into a first sensing electrode group and a second sensing electrode group, the first sensing electrode group is located on a first side of the reference electrode, and the second sensing electrode group is located on a second side of the reference electrode; and
a signal processing device coupled to the physiological signal sensing device to receive the at least one physiological signal, wherein the signal processing device compares the at least one physiological signal with a reference physiological signal pattern to obtain a comparison result, the signal processing device selects a selected electrode pair from the sensing electrodes based on the comparison result, and the signal processing device uses the selected electrode pair to perform a physiological signal measurement on the organism during a normal operation period,
wherein the selected electrode pair comprises a first selected electrode and a second selected electrode, the first selected electrode is selected from the first sensing electrode group and the second selected electrode is selected from the second sensing electrode group, the first selected electrode and the second selected electrode serve as the selected electrode pair,
wherein the at least one physiological signal includes at least two physiological signals, the signal processing device compares the at least two physiological signals with the reference physiological signal pattern in order to select a plurality of candidate physiological signals from the at least two physiological signals, the signal processing device selects two candidate physiological signals having a maximum and a second largest signal features, respectively, from the candidate physiological signals as two selected signals, and the signal processing device selects two sensing electrodes corresponding to the two selected signals from the plurality of sensing electrodes as the selected electrode pair,
wherein the signal processing device sorts a plurality of candidate electrodes corresponding to the plurality of candidate physiological signals in the plurality of sensing electrodes according to a plurality of signal features of the plurality of candidate physiological signals to determine a selection order, the signal processing device selects a first candidate electrode of a first order in the selection order and a second candidate electrode of a second order in the selection order as the selected electrode pair, and when a signal feature of the first candidate electrode or the second candidate electrode is lower than the signal feature of a third candidate electrode of a third order in the selection order, the signal processing device selects the third candidate electrode to replace the first candidate electrode or the second candidate electrode.

2. The physiological signal sensing system according to claim 1, wherein the at least one physiological signal comprises an electromyography signal of a muscle bundle of the organism.

3. The physiological signal sensing system according to claim 1, further comprises:
a switch coupling to the physiological signal sensing device to select one sensing electrode from the first sensing electrode group, or to select the one sensing electrode from the second sensing electrode group.

4. The physiological signal sensing system according to claim 1, further comprises:
a database for storing at least one reference pattern, wherein the signal processing device selects the reference physiological signal pattern from the at least one reference pattern of the database according to a target condition.

5. The physiological signal sensing system according to claim 1, wherein the signal processing device obtains a similarity by comparing any of the at least one physiological signal pattern with the reference signal pattern, and when the similarity is greater than a threshold value, the physiological signal having the similarity greater than the threshold value is selected as a candidate physiological signal.

6. A physiological signal sensing method, comprising:
sensing at least one physiological signal of an organism by a plurality of sensing electrodes of a physiological signal sensing device, wherein the physiological signal sensing device further comprises a reference electrode, and the plurality of sensing electrodes are located around the reference electrode and are divided into a first sensing electrode group and a second sensing electrode group, the first sensing electrode group is located on a first side of the reference electrode, and the second sensing electrode group is located on a second side of the reference electrode;
comparing the at least one physiological signal with a reference physiological signal pattern to obtain a comparison result by a signal processing device;
selecting a selected electrode pair from the sensing electrodes based on the comparison result by the signal processing device; and
performing a physiological signal measurement of the organism by using the selected electrode pair during a normal operation period by the signal processing device,
wherein the selected electrode pair comprises a first selected electrode and a second selected electrode, the first selected electrode is selected from the first sensing electrode group and the second selected electrode is selected from the second sensing electrode group, the first selected electrode and the second selected electrode serve as the selected electrode pair,
wherein the step of selecting the selected electrode pair from the sensing electrodes comprises:
comparing the at least one physiological signal with the reference physiological signal pattern in order to select a plurality of candidate physiological signals from the at least one physiological signal by the signal processing device, wherein the at least one physiological signal includes at least two physiological signals;

selecting two candidate physiological signals having a maximum and a second largest signal features, respectively, from the candidate physiological signals as two selected signals by the signal processing device; and selecting two sensing electrodes corresponding to the two selected signals from the plurality of sensing electrodes as the selected electrode pair by the signal processing device, wherein the step of selecting the selected electrode pair from the sensing electrodes further comprises:

sorting a plurality of candidate electrodes corresponding to the plurality of candidate physiological signals in the plurality of sensing electrodes according to a plurality of signal features of the candidate physiological signals to determine a selection order by the signal processing device;

selecting a first candidate electrode of a first order in the selection order and a second candidate electrode of a second order in the selection order as the selected electrode pair by the signal processing device; and selecting a third candidate electrode to replace the first candidate electrode or the second candidate electrode when a first signal feature of the first candidate electrode or a second signal feature of the second candidate electrode is lower than a third signal feature of a third candidate electrode of a third order in the selection order by the signal processing device.

7. The physiological signal sensing method according to claim 6, wherein the step of selecting the plurality of candidate physiological signals comprises:

obtaining a similarity by comparing any of the at least one physiological signal to the reference physiological signal pattern by the signal processing device; and selecting the physiological signal as the candidate physiological signal when the similarity is greater than a threshold value by the signal processing device.

8. A physiological signal sensing system, comprising:

a physiological signal sensing device having a plurality of sensing electrodes and a reference electrode, and the plurality of sensing electrodes are located around the reference electrode, wherein the sensing electrodes are used to contact a skin of an organism to sense at least one physiological signal, and the plurality of sensing electrodes are divided into a first sensing electrode group and a second sensing electrode group, the first sensing electrode group is located on a first side of the reference electrode, and the second sensing electrode group is located on a second side of the reference electrode; and a signal processing device coupling to the physiological signal sensing device to receive the at least one physiological signal, the signal processing device sorts a part or all of the sensing electrodes according to the at least one physiological signal to determine a selection order, the signal processing device selects a first sensing electrode of a first order in the selection order and a second sensing electrode of a second order in the selection order as the selected electrode pair, and the signal processing device uses the selected electrode pair to perform a physiological signal measurement on the organism during a normal operation period, wherein the selected electrode pair comprises a first selected electrode and a second selected electrode, the first selected electrode is selected from the first sensing electrode group and the second selected electrode is selected from the second sensing electrode group, the first selected electrode and the second selected electrode serve as the selected electrode pair, wherein the signal processing device selects a third sensing electrode to replace the first sensing electrode or the second sensing electrode when a first signal feature of the first sensing electrode or a second signal feature of the second sensing electrode is lower than a third signal feature of the third sensing electrode of a third order in the selection order.

* * * * *